United States Patent [19]

Baldwin et al.

[11] 4,411,899

[45] Oct. 25, 1983

[54] SUBSTITUTED DERIVATIVES OF AMINO ALKANE DIOLS AS GASTRIC SECRETION INHIBITORS

[75] Inventors: John J. Baldwin, Gwyneed Valley; William C. Lumma, Jr., Pennsburg, both of Pa.

[73] Assignee: Merck & Co., Inc., Rahway, N.J.

[21] Appl. No.: 332,691

[22] Filed: Dec. 21, 1981

[51] Int. Cl.$^3$ ................ C07D 285/10; A61K 31/425; A61K 31/535
[52] U.S. Cl. .............................. 424/246; 424/248.51; 424/250; 424/267; 424/270; 544/58.7; 544/134; 544/367; 546/209; 548/135; 260/245.5
[58] Field of Search ...................... 544/58.7, 134, 367; 546/209; 548/135; 424/246, 248.51, 250, 267, 270; 260/245.5

[56] References Cited

U.S. PATENT DOCUMENTS 3,950,333 4/1976 Durant et al. ...................... 424/256
4,128,658 12/1978 Price et al. .......................... 424/285

FOREIGN PATENT DOCUMENTS 875846 10/1979 Belgium .
3640 8/1979 European Pat. Off. .

OTHER PUBLICATIONS

Derwent Abstract 79110B/44.

Primary Examiner—Robert W. Ramsuer
Attorney, Agent, or Firm—Gabriel Lopez; Salvatore C. Mitri; Hesna J. Pfeiffer

[57] ABSTRACT

There are disclosed substituted derivatives of amino alkane diols and related compounds as well as processes for the preparation of such compounds. These compounds are useful for the suppression of gastric acid secretions in mammals and compositions for such uses are also disclosed.

12 Claims, No Drawings

SUBSTITUTED DERIVATIVES OF AMINO ALKANE DIOLS AS GASTRIC SECRETION INHIBITORS

BACKGROUND OF THE INVENTION

Inhibitors of gastric acid secretion functioning by antagonism of the histamine H2-receptor are effective antiulcer agents. Structurally, such components are typically viewed as molecules having three substituents or fragments; i.e., A-B-C, each of which can independently affect the antisecretory activity. The "A" portion may be a substituted or unsubstituted aromatic or heteroaromatic group such as are disclosed in, for example, U.S. Pat. No. 3,950,333 to Durant et al., U.S. Pat. No. 4,128,658 to Price et al. and Belgian Pat. No. 867,106 (Derwent Abstract 84065A/47).

The central, or "B" portion, may be a connecting chain joined to A such as A—$CH_2SCH_2CH_2$—, $AOCH_2CH_2CH_2$, or A—(m-phenylene)— as disclosed in the aforementioned patents as well as in European Pat. No. 3,640 to Jones et al. (Derwent Abstract 61827 B/34).

The remaining terminal substituent "C" is structurally distinct from either the A and B portions and may be, for example, a substituted guanidine, a substituted 1,1-diamino ethylene, a 3,5-diamino-1-alkyl triazole, or a substituted pyrimidinone as disclosed in the aforementioned U.S. Patents to Durant et al. and Price et al. as well as in Belgian Pat. No. 875,846 (Derwent Abstract 79110 B/44).

The present invention is directed to unique "B" moieties which confer antisecretory activity when combined with the A-C molecular fragments comprising these antiulcer agents.

SUMMARY OF THE INVENTION

This invention is concerned with substituted derivatives of amino alkane diols wherein the hydroxyl or derivatized hydroxyl function is a novel, structural feature not disclosed in the prior art.

DESCRIPTION OF THE INVENTION

The compounds of this invention are represented by the following structural formula:

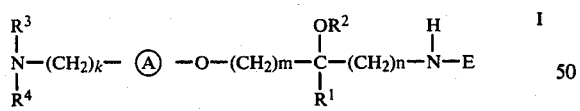

wherein:
$R^1$ is hydrogen, loweralkyl;
$R^2$ is hydrogen, loweralkyl, benzyl, loweralkanoyl, loweralkoxyloweralkyl, benzyloxyloweralkyl;
$R^3$ and $R^4$ are independently hydrogen, loweralkyl, cycloloweralkyl of $C_3$-$C_8$, cycloalkylalkyl of $C_3$-$C_8$, or $R^3$ and $R^4$ may be joined to form, together with the nitrogen to which they are attached, —$(CH_2)_rX(CH_2)_{r'}$—wherein X can be O, S, $CH_2$, or $NR^5$ wherein $R^5$ is hydrogen, loweralkyl; loweralkanoyl;
r and r' are independently 1, 2, or 3 provided that when r or r' is 1, X is $CH_2$;
n is 1 or 2;
m is 1 or 2;
k is 0 to 4;

Ⓐ is a substituted phenylene wherein the substituent can be hydrogen, halo, cyano, loweralkoxy, loweralkyl; or, a 6-membered heterocycle containing one to three nitrogen atoms and optionally bearing substituent(s) $R_1^6$ wherein 1 is 0–2 and $R^6$ is halo (fluoro, chloro, bromo), hydrogen, loweralkyl, $CO_2R^7$, CN, O=$CNHR^7$ wherein $R^7$ is as defined below; or, a 5-membered heterocycle containing two to three heteroatoms selected from oxygen, sulfur or nitrogen with the proviso that when either an oxygen or a sulfur atom is present, the remaining heteroatom(s) must be nitrogen, and optionally bearing substituent(s) $R_1^6$ wherein 1 is 0–1 and $R^6$ is as defined above;

E is a group having the following formulae:

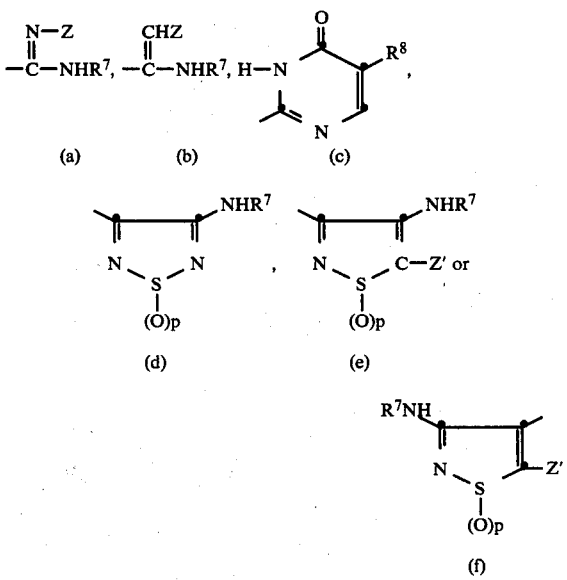

wherein:
$R^7$ is hydrogen, loweralkyl, substituted loweralkyl wherein the substituent can be hydroxy, alkoxy, loweralkynyl, loweralkenyl or loweralkanoyl; aryl; substituted aryl wherein the substituent can be halo, loweralkoxy, loweralkyl; heteroaryl;
$R^8$ is $CH_2$-aryl, $CH_2$-substituted aryl or $CH_2$-disubstituted aryl wherein the substituents can be halo, alkoxy, loweralkyl, —$OCH_2O$—; —$CH_2$-pyridyl or —$CH_2$-substituted pyridyl wherein the substituents can be amino, loweralkyl;
Z is CN, $NO_2$, $CO_2R^3$, O=CN—$R^3R^4$, $SO_2$-N—$R^3R^4$ wherein $R^3$ and $R^4$ are as defined above;
Z' is CN, $CO_2R^3$, O=CN—$R^3R^4$ wherein $R^3$ and $R^4$ are as defined above;
p is 1 or 2; and,
the physiologically acceptable, non-toxic salts thereof.

In the instant invention, unless specified otherwise, the term "loweralkyl" and "loweralkoxy" are intended to include those alkyl groups containing from 1 to 5 carbon atoms in either a straight or branched configuration. Examples of such alkyl groups are methyl, ethyl, propyl, iso-propyl, butyl, sec-butyl, pentyl and the like.

The term "cycloloweralkyl" is intended to include those cycloalkyl groups of from 3 to 7 carbon atoms. Examples of such cycloalkyl groups are cyclopropyl, cyclobutyl, cyclopentyl, cyclohexyl, and cycloheptyl.

The term "loweralkanoyl" is intended to include such groups as formyl, acetyl, propionyl and branched chain analogs containing 1 to 6 carbon atoms.

The term "heteroaryl" includes five or six membered rings having one or two heteroatoms selected from O, N or S.

The term "loweralkynyl" is intended to include those alkynyl groups of from 3 to 5 carbon atoms of either a straight or branched configuration, and one triple bond. Examples of such alkynyl groups are propargyl, butynyl, pentynyl, and the like.

Ⓐ in the compounds of this invention includes phenylene, imidazole, thiazole, thiadiazole, oxazole, pyrazine, pyrimidine, pyridine, oxadiazole, and the like.

In Formula I preferred compounds are realized when Ⓐ is m-phenylene.

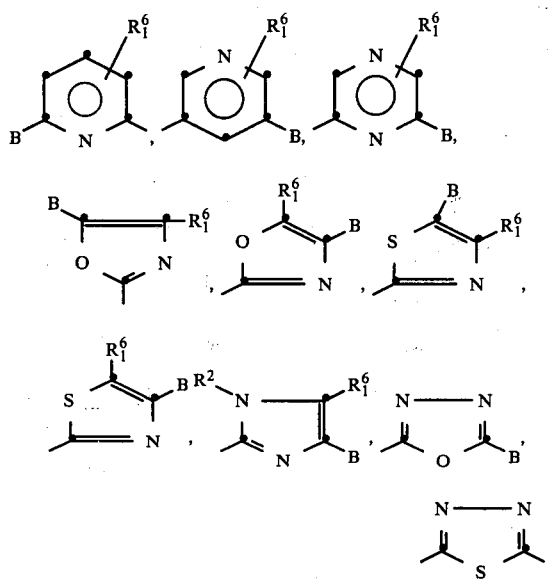

wherein $R^2$ and $R^6$ are as defined above and B is —$(CH_2)_k$N—$R^3R^4$ wherein k, $R^3$ and $R^4$ are as defined above. A can also be a benzofused 5- or 6-membered heterocycle containing 2 heteroatoms selected from O, N, and S with the proviso that when either an oxygen or a sulfur atom is present, the remaining heteroatom is nitrogen.

Specific examples of the preferred compounds of this invention are:

(1) N-3-[4-methyl-5-(dimethylaminomethyl)-2-imidazolyloxy]-2-hydroxypropyl-N'-methyl-N''-cyanoguanidine.
(2) 3-[3-[4-methyl-5-(dimethylaminomethyl)-2-imidazolyoxy]-2-hydroxypropylamino]-4-amino-1,2,5-thiadiazole-1,1-dioxide.
(3) 3-[3-[4-methyl-5-(dimethylaminomethyl)-2-imidazolyloxy]-2-hydroxypropylamino]-4-amino-1,2,5-thiadiazole-1-oxide.
(4) 3-[3-[4-methyl-5-(dimethylaminomethyl)-2-imidazolyloxy]-2-methoxypropylamino]-4-amino-1,2,5-thiadiazole-1-oxide.
(5) 3-[3-[4-methyl-5-(dimethylaminomethyl)-2-imidazolyloxy]-2-hydroxypropylamino]-4-amino-5-ethoxycarbonylisothiazole-1,1-dioxide.
(6) 3-[3-[4-methyl-5-(dimethylaminomethyl)-2-imidazolyloxy)-2-hydroxypropylamino]-4-amino-5-carbamoylisothiazole-1,1-dioxide.
(7) 4-[3-[4-methyl-5-(dimethylaminomethyl)-2-imidazolyloxy)-2-methyl-2-hydroxypropylamino]-3-amino-5-ethoxycarbonylisothiazole-1,1-dioxide.
(8) 1-N-[-3-[4-methyl-5(dimethylaminomethyl)-2-imidazolyloxy]-2-hydroxypropyl]amino-1-N-methylamino-2-nitroethene.
(9) 2-[3-[4-methyl-5-(dimethylaminomethyl)-2-imidazolyloxy]-2-hydroxypropylamino]-5-(6-methyl-3-pyridylmethyl)pyrimidin-4(3H)-one.
(10) N-[3-[4-(dimethylaminomethyl)-2-thiazolyloxy]-2-hydroxypropyl]-N'-[1-prop-2-ynyl]-N''-cyanoguanidine.
(11) N-[3-[4-(dimethylaminomethyl)-2-thiazolyloxy]-2-hydroxypropyl]-N'-sulfamoyl guanidine.
(12) 1-[N-[3-[4-(dimethylaminomethyl)-2-thiazolyloxy]-2-hydroxypropyl]amino]-1-N-methylamino-2-nitroethene.
(13) 3-[3-[4-(dimethylaminomethyl)-2-thiazolyloxy]-2-hydroxypropylamino]-4-amino-5-sulfamoylisothiazole-1,1-dioxide.
(14) 3-[3-[4-(morpholinomethyl)-2-thiazolyloxy)-2-hydroxypropylamino]-4-amino-5-carbamoyl-isothiazole-1-oxide.
(15) 3-[3-[5-(dimethylaminomethyl)-2-thiazolyloxy]-2-(benzyloxy)propylamino]-4-amino-5-cyanoisothiazole-1,1-dioxide.
(16) 3-[3-[5-(dimethylaminomethyl)-2-thiazolyloxy]-2-hydroxypropylamino]-4-amino-1,2,5-thiadiazole-1,1-dioxide.
(17) 5-[3-[4-dimethylaminomethyl-2-thiazolyloxy]methyl]oxazolidine-2(3H)-one.
(18) 2-[3-[4-(piperidinylmethyl)-2-thiazolyloxy]-2-hydroxypropylamino]-5-(4-chlorobenzyl)pyrimidin-4-(3H)-one.
(19) 3-[3-[3-(dimethylaminomethyl)phenoxy]-2-hydroxypropylamino]-4-amino-1,2,5-thiadiazole-1-oxide.
(20) 3-[3-[3-(dimethylaminomethyl)phenoxy]-2-hydroxypropylamino]-4-amino-1,2,5-thiadiazole-1,1-dioxide.
(21) N-[3-[3-(dimethylaminomethyl)phenoxy]-2-hydroxypropyl]-N'-sulfamoylguanidine.
(22) 1-[N-[3-[3-(N-methylpiperazinylmethyl)phenoxy]-2-hydroxypropyl]amino]-1-N-methylamino-2-nitroethene.
(23) 3-[3-[3-(cyclopropylaminomethyl)phenoxy]-2-hydroxypropylamino]-4-amino-5-carboethoxyisothiazole-1,1-dioxide.
(24) 3-[3-[6-(morpholinomethyl)-2-pyridyloxy]-2-hydroxypropylamino]-4-methylamino-5-cyanoisothiazole-1,1-dioxide.
(25) 3-[3-[3-(pyrrolidinomethyl)phenoxy]-2-acetoxypropylamino]-4-amino-5-carboethoxyisothiazole-1,1-dioxide.
(26) N-[3-[6-(dimethylaminomethyl)-2-pyridyloxy]-2-hydroxypropyl]-N'-methyl-N''-cyanoguanidine.
(27) N-[3-[6-(N,N-dimethylaminomethyl-2-benzoxazolyloxy]-2-hydroxy-1-propyl]-amino-N'-methyl-N''-cyanoguanidine.

The compounds according to the invention readily form physiologically acceptable salts. Such salts include salts with inorganic acids such as hydrochlorides, hydrobromides, sulfates, nitrates and phosphates. Particularly useful salts of organic acids are formed with aliphatic mono- or dicarboxylic or sulfonic acids. Examples of such salts are acetates, maleates fumarates, tartrates, citrates, benzoates, succinates, methane sulfonates, and isethionates. The compounds and their salts may also form hydrates and solvates. In addition, the nitrogen atom in the group

may also form quaternary salts and N-oxides.

It will also be appreciated by those skilled in the art that the compounds of this invention will have a tautomeric isomerism about the nitrogen atoms of the E groups. Where one or both of the adjacent nitrogen atoms has a hydrogen atom thereon, the following imino structures may be formed:

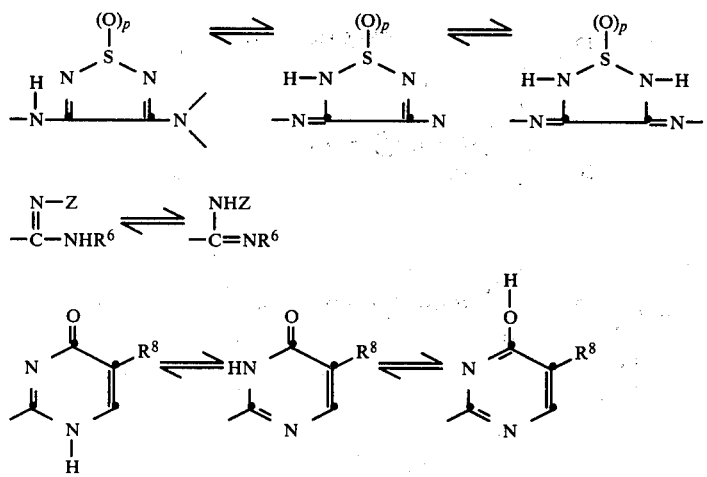

All of the various tautomeric structures of the instant compounds are intended to be included in this invention.

In addition, when p is 1, there exists the possibility of stereoisomerism in the instant compounds, corresponding to an R or S absolute configuration at the sulfur atom of the thiadiazoles and isothiazoles

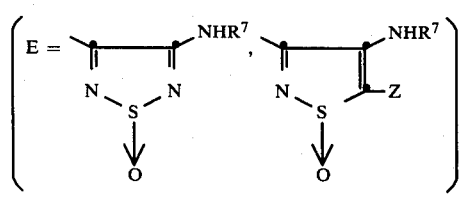

In addition, a chiral center exists at the carbon of the connecting chain bearing $OR^2$. It is intended that all such stereoisomers are included within the instant invention.

Further, in those cases where HNE is a guanidine or diaminoethane moiety, the possibility of geometrical isomerism exists; viz, Z and E isomers of these compounds which are also included within the instant invention.

As stated above, the compounds represented by Formula I, have been found to have pharmacological activity in the animal body as antagonists to certain actions of histamine which are not blocked by "antihistamines" such as mepyramine. For example, they have been found to inhibit selectively the histamine-stimulated secretion of gastric acid in the stomach of chronic fistula dogs at doses of from 0.03 to 1.0 mg per kilogram intravenously or orally from 0.1 to 3.0 mg per kilogram. Similarly, the action of these compounds is demonstrated by their antagonism to the effects of histamine on other tissues which are not affected by histamine H1 antagonists. An example of such tissue is the isolated guinea-pig right atrium.

The pharmaceutical carrier employed may be for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. If a liquid carrier is used, the preparation may be in the form of a syrup, emulsion, soft gelatin capsule, sterile injectable liquid such as an ampoule, or an aqueous of nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an effective amount to inhibit histamine gastric acid secretory activity. The route of administration may be orally or parenterally.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those mentioned above.

The compounds of this invention can also be employed with other pharmacologically active compounds. Exemplary of such other pharmacological compounds are anticholinergic agents such as propantheline; H 1 antihistamines such as mepyramine, pyribenzamine chlorpheniramine, and the like; prostanoids such as prostaglandin E 1, prostaglandin A and the like; histidine decarboxylase inhibitors such as α-fluoromethylhistidine, Brocresin (3-hydroxy-4-bromobenzyloxyamine), α-hydrazinohistidine, and the like; antiulcer agents such as carbenoxolone, Vitamin U, and the like; antacids such as calcium carbonate preparations, aluminum hydroxide, and the like; nitrosation inhibitors such as Vitamin C; antigastrins such as somatostatin; as well as combinations and mixtures thereof.

Advantageously the composition will be made up in a dosage unit form appropriate to the desired mode of administration, for example as a tablet, capsule or injectable solution.

The methods that can be employed to prepare the compounds of this invention are shown in the following Reaction Schemes wherein $R^1$, $R^2$, $R^3$, $R^4$, $R^5$, $R^6$, $R^7$, $R^8$, (A), E, X, Z, k, l, m, n, and p are as defined above; M is an alkali or alkaline earth metal or quaternary ammonium; P is a suitable amine protecting group such as phthaloyl, aryloxycarbonyl, t-butyloxycarbonyl, loweralkanoyl, loweralkylsulfonyl, or P may be attached to both the N and O of the side chain in place of $R^2$ to form a 5- or 6-membered ring wherein P is

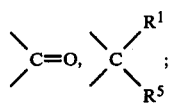

and, Y is loweralkoxy, halo (Cl, Br, I) loweralklthio, phenoxy, phenylthio, loweralkylsulfonyl, aryl, arylsulfonyl, or substituted arylsulfonyl wherein the substituent can be loweralkyl.

REACTION SCHEME I

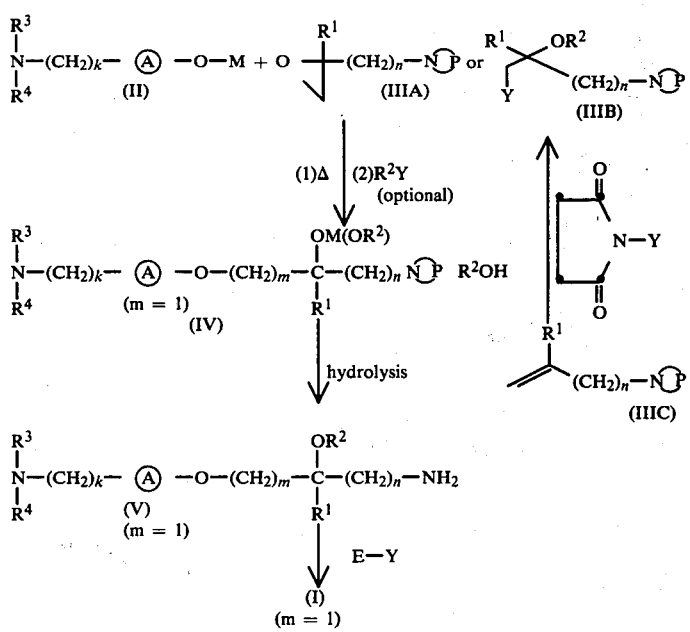

REACTION SCHEME II

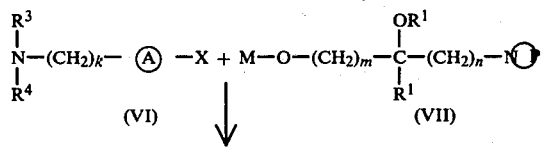

REACTION SCHEME II -continued

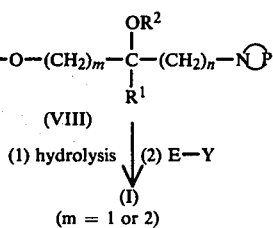

REACTION SCHEME III

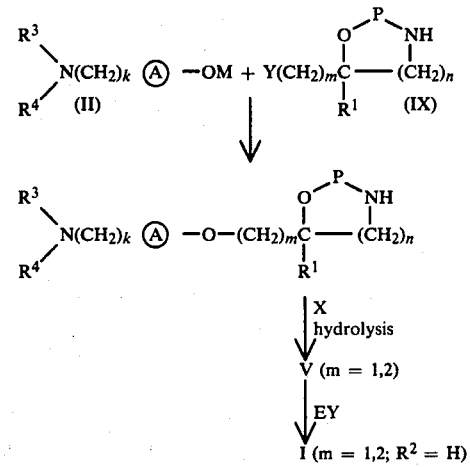

As shown in Reaction Scheme I, an appropriate salt II is generated from the A OH moiety of II with a catalytic amount of MOH or MH or with a tertiary amine such as pyridine at temperatures from 0° to 100° C. in a polar non protic solvent or neat in the absence of solvent. With MOH or MH, temperatures of 0°–25° are preferred, but with tertiary amines, the reaction is conducted at 80°–100° in the presence of epoxides IIIA and a catalytic amount of mineral acid.

Where IIIB is desired for use, it is synthesized by reaction of the olefin IIIC with N-halo phthalimide (or N-halosuccinimide) in $R^2OH$ as the solvent at 0°–50° C. and isolated by methods known to those skilled in the art. Intermediates IIIB are then reacted with II as described above to give IV.

The reaction of II with III is carried out at the appropriate temperature until the starting materials have completely reacted. The mixture is then worked up with aqueous base to give V ($R^2=H$) or with one equivalent of a base such as alkali or alkaline earth carbonate or tertiary amine and an appropriate acylating agent $R^2Y$ to give V ($R^2$=lower alkanoyl). This route affords V (m=1) which can be reacted with reagents EY in polar solvents such as lower alkanols, diloweralkyl loweralkanamides, nitroloweralkanes, and the like, to give compounds I.

In Reaction Scheme II, intermediates VI, in which the moiety Ⓐ is a heterocycle bearing an appropriate leaving group X, are reacted with salts VII, which are known in the art, to give intermediates VIII. The reaction is carried out in polar aprotic solvents such as DMF, acetonitrile, and the like, at temperatures of 75° to 150° C., preferably at 100° C. Hydrolysis to remove the protective group gives intermediates V whose conversion to compound I is described above.

In Reaction Scheme III, the salts II are reacted with intermediates IX (known in the art) in polar aprotic solvents at 25°–150° C., preferably at 75°–85°, to give intermediates X. The latter are hydrolyzed to compounds V which are converted to preferred compounds I as described above.

The following examples are provided in order that the invention might be more fully understood, but they are not to be construed as limitative of the invention. Unless otherwise indicated, all temperatures are in degrees Celsius.

EXAMPLE 1

3-(3-Chloro-2-hydroxypropoxy)benzaldehyde

A mixture of 3-hydroxybenzaldehyde (24.4 g, 0.2 mol), epichlorohydrin (47 ml) and pyridine (0.4 ml) is heated 5 hours on a steam bath. The crude mixture is partitioned between methylenechloride-water and the $CH_2Cl_2$ extract washed with dilute aqueous $NaHCO_3$, dried ($Na_2SO_4$), filtered and concentrated in vacuo to give the crude title product. Distillation gives a colorless oil bp 160° (0.2 mm); 21.2 g.

EXAMPLE 2

3-(3-Phthalimido-2-hydroxypropoxy)benzaldehyde

The distilled product from Example 1 (21.1 g, 0.098 mol) and potassium phthalimide (37 g, 0.20 mol) are dissolved in 100 ml of N,N-dimethylformamide and the mixture is heated 22 hours on a steam bath under $N_2$. The mixture is cooled, diluted with 200 ml of ether and filtered. The filtrate is concentrated to remove ether and diluted to 500 ml with water to give the crystalline title product, 30.8 g, mp 122°–126°.

EXAMPLE 3

3-(3-Amino-2-hydroxypropoxy)-N,N-dimethylbenzylamine

A solution of dimethylamine hydrochloride (2.14 g, 26.2 mmol) and KOH (0.4 g) in 50 ml $CH_3OH$ is treated with the product from Example 2 (6.0 g, 19.4 mmol). The resulting white suspension is then treated with sodium cyanoborohydride (0.68 g, 0.011 mol) at room temperature. The pH gradually rises and is maintained at 2–4 by addition of conc. hydrochloric acid from a micro pipette. After 3 hours, the mixture is concentrated in vacuo and the residue partitioned between dilute aqueous HCl and $CH_2Cl_2$. The aqueous layer is separated and basified with aqueous methylamine and kept for 3 days at room temperature in a stoppered flask.

The mixture is heated to expel excess methylamine, cooled and extracted with $CH_2Cl_2$. The $CH_2Cl_2$ extracts are dried ($Na_2SO_4$), filtered and concentrated in vacuo to give 2.5 g of the title amino alcohol as an oil.

EXAMPLE 4

3-[3-(Dimethylaminomethyl)phenoxy-2-hydroxypropyl]amino-4-amino-1,2,5-thiadiazole-1-oxide The amino alcohol from Example 3 (0.50 g, 2.2 mmol) and 3-amino-4-ethoxy-1,2,5-thiadiazole-1-oxide (0.36 g, 2.2 mmol) are dissolved in 10 ml of isopropanol at room temperature under $N_2$. The mixture is stirred one hour at room temperature then filtered through glass wool. The filtrate is stirred 3 days at room temperature and filtered to give 0.45 g of the title product as an isopropanol solvate, mp 145° dec.

EXAMPLE 5

N-3-[3-(Dimethylaminomethyl)phenoxy-2-hydroxypropyl]-N'-methyl-N"-cyanoguanidine By a procedure analogous to Example 4, the amino alcohol from Example 3 can be reacted with one equivalent of N-cyano-N'-methyl, S-methylisothiourea to give the title compound.

EXAMPLE 6

2-Allyloxy-5-(N,N-dimethylcarbamoyl)thiazole

To a stirred suspension of 0.5 g (10 mmol) of sodium hydride in 5 ml of dry N,N-di-methylformamide under $N_2$, there can be added 0.6 g (10 mmol) of sieve-dried allyl alcohol. After hydrogen evolution ceases, the stirred solution can be treated with 2-bromo-5-(N,N-dimethylcarbamoyl)thiazole (2.35 g, 10.0 mmole). The mixture can then be stirred at 40° under $N_2$ for 18 hours, diluted with four volumes of water and extracted with ether. The ether extracts can be washed with water, dried ($Na_2SO_4$), filtered and concentrated in vacuo to give an oil which can then be distilled to give pure title compound.

EXAMPLE 7

2-(3-Bromo-2-hydroxypropoxy)-5-(N,N-dimethylcarbamoyl)thiazole

The product from Example 6 (2.12 g, 10.0 mmol) can be suspended in 10 ml of 50% aqueous N,N-dimethylformamide and the rapidly stirred suspension treated with solid N-bromosuccinimide (2.0 g, 11 mmol) in portions. After 1 hour, the mixture can be extracted with ether and the combined extracts washed with wa-

EXAMPLE 8

2-(3-Bromo-2-methoxypropoxy)-5-[N,N-dimethylcarbamoyl]thiazole

By a procedure analogous to Example 7 using 50% methanol-N,N-dimethylformamide as solvent, the title compound can be obtained as an oil.

EXAMPLE 9

2-(3-Phthalimido-2-hydroxypropoxy)-5-(N,N-dimethylcarbamoyl)thiazole

By a procedure analogous to Example 2 the product from Example 7 can be reacted with potassium phthalimide in N,N-dimethylformamide to give the solid title compound.

EXAMPLE 10

2-(3-Phthalimido-2-methoxypropoxy)-5-(N,N-dimethylcarbamoyl)thiazole

By a procedure analogous to Example 2, the product from Example 8 can be reacted with potassium phthalimide in N,N-dimethylformamide to give the solid title compound.

EXAMPLE 11

2-(3-Amino-2-hydroxypropoxy)-5-(N,N-dimethylcarbamoyl)thiazole

The product from Example 9 (4.0 g, 10.6 mmol) can be added to a solution of hydrazine (0.38 g, 12 mmol) in absolute ethanol (20 ml) and the suspension refluxed 4 hours under nitrogen on a steam bath. The mixture can then be cooled and filtered and the filtrate concentrated in vacuo to give the title compound as an oil.

EXAMPLE 12

2-(3-Amino-2-hydroxypropoxy)-5-(N,N-dimethylaminomethyl)thiazole

The product from Example 11 (2.0 g, 8.2 mmol) can be added to a solution of borane dimethylsulfide complex (2.5 g, 33 mmol) in 25 ml of dry tetrahydrofuran at room temperature. After one hour, the mixture can be heated to reflux for 4 hours under nitrogen. The resulting suspension can then be cooled to 0° C., cautiously treated dropwise with 5 ml of glacial acetic acid and, after hydrogen evolution ceases, the solution can be heated to reflux for 8 hours. The mixture can then be cooled to 0° C., cautiously treated with water and concentrated in vacuo. The aqueous residue can be extracted with ether, basified with 10 N sodium hydroxide and reextracted with methylene chloride-ethanol. The methylene chloride extracts can then be combined, dried ($Na_2SO_4$), filtered and concentrated in vacuo to give the crude product. The pure title compound can be obtained by chromatography on silica gel with 20% methanol in chloroform.

EXAMPLE 13

2-N-[3-[5-(N,N-Dimethylaminomethyl)-2-thiazolyl]-2-hydroxy-1-propyl]amino-N'-methylamino-1-nitroethene The amino alcohol from Example 12 (2.31 g, 10.0 mmol) can be added to a solution of 2-methylthio-2-N-methylamino-1-nitroethene (1.5 g, 10 mmol) in 10 ml of acetonitrile. The resulting mixture can then be stirred 24 hours at room temperature and the precipitated title compound collected by filtration.

EXAMPLE 14

2-[3-[5-(N,N-Dimethylaminomethyl)-2-thiazolyl]-2-hydroxy-1-propylamino]-5-(6-methyl-3-pyridylmethyl)-4-pyrimidone The amino alcohol from Example 12 (2.31 g, 10.0 mmol) can be added to a solution of 5-(6-methyl-3-pyridyl-methyl-2-methylthio-4-pyrimidone (2.5 g, 10.0 mmol) in 25 ml of dry pyridine and the mixture refluxed 72 hours under nitrogen. The mixture can then be concentrated under vacuum and the residue diluted with water and extracted with ethyl acetate (hot). The ethyl acetate extracts can be cooled to give the solid title compound.

EXAMPLE 15

3-(2,2-Dimethoxy-1-propoxy)N,N-dimethylbenzamide

3-Hydroxybenzamide can be added to a stirred suspension of sodium hydride (1.0 g 50% in nujol, 20 mmol) in 20 ml of dry N,N-dimethylformamide under $N_2$. The mixture can then be stirred until hydrogen evolution ceases and then treated with 1-bromo-2,2-dimethoxy propane at room temperature. After refluxing 10 hours, the mixture can be diluted with water to obtain the title compound.

EXAMPLE 16

1-[(3-N,N-Dimethylaminomethyl)phenoxy]-2-propanone

The product from Example 15 can be reduced with borane dimethylsulfide complex in tetrahydrofuran at reflux for 12 hours followed by hydrolysis with 2 N aqueous hydrochloric acid on a steam bath to give the title compound after basification to pH 10 and extraction with ether.

EXAMPLE 17

5-[3-(N,N-Dimethylaminomethyl)phenoxy]methyl-5-methyloxazolidine 2-thione

The product of Example 16 can be converted to the title compound by the procedure of T. Agawa, et al., Angew. Chem. Int. Ed. Engl. 20, 1981, 126.

EXAMPLE 18

3-[3-(N,N-Dimethylaminomethyl)phenoxy]-2-hydroxy-2-methyl-1-propylamine

The product from Example 17 can be hydrolyzed by refluxing in 5 N sodium hydroxide under nitrogen for 24 hours to give the title compound.

EXAMPLE 19

N-[3-[3-(N,N-Dimethylaminomethyl)phenoxy]-2-hydroxy-2-methyl-1-propyl]amino-4-amino-5-ethoxycarbonylisothiazole-1,1-dioxide The product from Example 8 can be reacted with one equivalent of 3-ethoxy-4-amino-5-ethoxycarbonylisothiazole-1,1-dioxide in acetonitrile at room temperature for 24 hours to give the solid title compound.

The following examples illustrate the preparation of intermediates used to prepare the compounds of this invention.

PREPARATION 1

Ethoxycarbonylmethane Sulfonamide

A solution of 54.6 g (0.29 mole) ethoxy carbonyl methanesulfonyl chloride in 250 ml methylene chloride is stirred at 0° under a nitrogen atmosphere while 46.8 g (0.29 mole) hexamethyldisilazane is added dropwise. The resulting cloudy solution is allowed to warm to 25° over one hour and then evaporated in vacuo to an oil which crystallizes: yield of the title product is 48.4 g (100%), mp 63°–67°; lit.[1] mp 67°–68°, lit[2] mp 66°–68°.

[1] *JACS* 1959, 81, 5655 R. L. Hinman, L. Locatelli, Jr.
[2] *Bull. Soc. Chim. Fr.* 1975 (3–4), 807 A. LeBerre, A. Etienne, B. Desmazieres

PREPARATION 2

Disodium salt of 3,4-Dihydroxy-5-ethoxycarbonylisothiazole-1,1-dioxide

A solution of sodium ethoxide is prepared from 7.6 g (0.33 g-atom) sodium (spheres) in 200 ml abs. ethanol under a nitrogen atmosphere. At 25° a solution of 27.6 g (0.165 mole) ethoxycarbonyl methane sulfonamide in 200 ml ethanol is added to the ethoxide solution, following which is added dropwise a solution of 24.1 g (0.165 mole) diethyloxalate in 50 ml ethanol. The resulting thick suspension is warmed to reflux and stirred under reflux overnight. The mixture is cooled to 25°, filtered and the white solid washed with 100 ml abs. ethanol. The disodium salt, 41.4 g (95%), may be recrystallized from 95% ethanol. The salt is stable as a hemihydrate (after drying at 95°/0.3 mm Hg over $P_2O_5$ for 24 hours); mp 265°–285° (dec).

Anal. Calcd. for $C_6H_5NO_6SNa_2 \cdot \frac{1}{2}H_2O$: C, 26.28; H, 2.21; N, 5.11. Found: C, 26.08; H, 2.49; N, 5.12.

PREPARATION 3

3-Ethoxy-4-chloro-5-ethoxycarbonyl isothiazole-1,1-dioxide

In a dry flask fitted with a magnetic stirrer, condenser and calcium sulfate drying tube are placed 3.2 g (0.011 mole) of the Example 2 disodium salt and 11.0 g (0.053 mole) phosphorous pentachloride. The flask is immersed in a preheated 100° oil bath and the mixture is stirred for 18 hours, following which phosphorous oxychloride is distilled off under aspirator pressure. The solid residue is slurried in 100 ml ether, the ether supernatant filtered rapidly into a clean, dry flask containing 15 ml absolute ethanol. The ether extraction of the residual solid is repeated three times with all ether-ethanol filtrates combined. After stirring at room temperature for 30 minutes, the ether-ethanol solution is concentrated in vacuo to an oily solid which can be collected by suction filtration after trituration with a small amount of ether. This solid title compound weighs 890 mg (30%); mp 134°–136°, MS:m/e 267 (M+), 222 (M—$OC_2H_5$), 135 (M—$OC_2H_5$—[Cl—C≡C—C—O+]), 87 (Cl—C≡C—C—O+).

Anal. Calcd. for $C_8H_{10}ClNO_5S$: C, 35.90; H, 3.77; N, 5.23. Found: C, 35.70; H, 3.84; N, 5.48.

PREPARATION 4

3,4-Diethoxy-5-ethoxycarbonyl isothiazole-1,1-dioxide

Triethylamine (1.05 ml, 7.5 mmol) dissolved in 10 ml methylene chloride is added dropwise to a stirred solution of 2.0 g (7.5 mmol) of the Example 3 compound and 2.5 ml absolute ethanol in 10 ml methylene chloride at 0° C. When the addition is complete, the resulting solution is stirred an additional 30 minutes and then evaporated at 35° in vacuo to an oil. Chromatography over silica gel (elutant, methylene chloride) produces tlc homogenous, title material, 1.6 g (80%), mp 129°–133°.

Anal. Calcd. for $C_{10}H_{15}NO_6S$: C, 43.31; H, 5.45; N, 5.05. Found: C, 43.21; H, 5.60; N, 5.30.

PREPARATION 5

3-Ethoxy-4-amino-5-ethoxycarbonyl isothiazole-1,1-dioxide

Under a nitrogen atmosphere a solution of 1.41 g (5.3 mmol) of the Example 3 compound in 15 ml of methylene chloride is stirred in an ice bath while a solution of 1.2 g (7.9 mmol) hexamethyldisilazane in 10 ml methylene chloride is added dropwise. The solution is allowed to warm to room temperature at which temperature stirring is continued for 18 hours. The solution is then evaporated in vacuo to an oil which is redissolved in 20 ml of a mixture of methylene chloride (15)-ethanol (5). After stirring at room temperature for one hour, the solution is again concentrated in vacuo, leaving a solid, 1.1 g (85%), mp 163°–165°. Recrystallization from ethyl acetate provides analytically pure title compound, mp 172.5°–173°.

Anal. Calcd. for $C_8H_{12}N_2O_5S$: C, 38.71; H, 4.87; N, 11.28. Found: C, 38.76; H, 4.91; N, 11.40.

The title compound can also be prepared by an alternate route employing the Example 4 compound and hexamethyldisilazane following the above procedure.

From 690 mg (2.5 mmole) of the Example 4 compound and 600 mg (3.75 mmole) hexamethyldisilazane there is obtained 525 mg (85%) of the title compound, mp 168°–172°. Thin layer chromatography (silica GF, 95:5 $CHCl_3:CH_3OH$) shows this to be identical with the material prepared from the 3-ethoxy-4-chloro-compound; a mixed melting point is undepressed (169°–173°).

What is claimed is:

1. A compound having the formula:

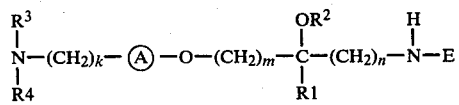

wherein $R^1$ is hydrogen, loweralkyl;

$R^2$ is hydrogen, loweralkyl, benzyl, loweralkanoyl, loweralkyoxyloweralkyl, benzyloxyloweralkyl;

$R^3$ and $R^4$ are independently hydrogen, loweralkyl, cycloloweralkyl of $C_3$–$C_8$, cycloalkylalkyl of $C_3$–$C_8$, or $R^3$ and $R^4$ may be joined to form, together with the nitrogen to which they are attached, —$(CH_2)_rX(CH_2)_{r'}$— wherein X can be O, S, $CH_2$, or $NR^5$ wherein $R^5$ is hydrogen, loweralkyl; loweralkanoyl;

r and r' are independently 1, 2, or 3 provided that when r or r' is 1, X is $CH_2$;

n is 1 or 2;

m is 1 or 2;

k is 0 to 4;

Ⓐ is a substituted phenylene wherein the substituent can be hydrogen, halo, cyano, loweralkoxy, loweralkyl;

E is

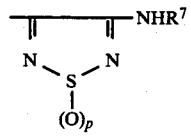

wherein
R[7] is hydrogen, loweralkyl, substituted loweralkyl wherein the substituent can be hydroxy, alkoxy; loweralkynyl; loweralkenyl or loweralkanoyl; aryl; substituted aryl wherein the substituent can be halo, loweralkoxy, loweralkyl; heteroaryl;
p is 1 or 2; and,
the physiologically acceptable, non-toxic salts thereof.

2. A compound of claim 1 wherein R[1] is hydrogen, loweralkyl; and, R[2] is hydrogen, loweralkyl, substituted loweralkyl wherein the substituent is loweralkoxy or loweralkanoyl.

3. A compound of claim 2 wherein Ⓐ is m-phenylene and k is 1.

4. A compound of claim 2 wherein E is:

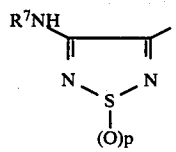

wherein R[7] is hydrogen, loweralkyl, or substituted loweralkyl wherein the substituent is loweralkenyl, loweralkynyl, loweralkanoyl, loweralkoxy; and, p is 1 or 2.

5. A compound of claim 4 which is: 3-[3-[3-(dimethylaminomethyl)phenoxy]-2-hydroxypropyl]amino-4-amino-1,2,5-thiadiazole-1-oxide.

6. A compound of claim 4 which is: 3-[3-[3-(dimethylaminomethyl)phenoxy]-2-hydroxypropyl]amino-4-amino-1,2,5-thiadiazole-1,1-dioxide.

7. A composition useful for suppressing gastric acid secretions in an animal with excess gastric acid secretions which comprises an inert carrier; and, an antisecretorily effective amount of a compound of claim 1.

8. A composition useful for suppressing gastric acid secretions in an animal with excess gastric acid secretions which comprises an inert carrier; an effective antisecretory amount of a compound of claim 1; and, a pharmacologically active compound which is a member of the group consisting of propantheline, mepyramine, pyribenzamine, chlorpheniramine, prostaglandins, α-fluoromethylhistidine, 3-hydroxy-4-bromobenzyloxyamine, α-hydrazino histidine, carbenoxolone, Vitamin U, calcium carbonate preparations, aluminum hydroxide, Vitamin C, somatostatin, and combinations and mixtures thereof.

9. A composition useful for suppressing gastric acid secretions in an animal with excess gastric acid secretions which comprises an inert carrier; an antisecretorily effective amount of a compound of claim 1; and, α-fluoromethyl histidine.

10. A method for suppressing gastric acid secretions in an animal with excess gastric acid secretions which comprises administering to said animal an effective antisecretory amount of a compound of claim 1.

11. A method for suppressing gastric acid secretions in an animal with excess gastric acid secretions which comprises administering to said animal an antisecretorily effective amount of a compound of claim 1; and, a pharmacologically active compound which is a member of the group consisting of propantheline, mepyramine, pyribenzamine, chlorpheniramine, prostaglandins, α-fluoromethylhistidine, 3-hydroxy-4-bromobenzyloxyamine, α-hydrazino histidine, carbenoxolone, Vitamin U, calcium carbonate preparations, aluminum hydroxide, Vitamin C, somatostatin, and combinations and mixtures thereof.

12. A method for suppressing gastric acid secretions in an animal with excess gastric acid secretions which comprises administering to said animal an antisecretorily effective amount of a compound of claim 1; and, α-fluoromethyl histidine.

* * * * *